(12) United States Patent
Swanson et al.

(10) Patent No.: US 7,833,474 B2
(45) Date of Patent: Nov. 16, 2010

(54) STERILE DEVICE AND METHOD FOR PRODUCING SAME

(75) Inventors: Aaron J. Swanson, Los Angeles, CA (US); Jennifer M. Reynolds, Simi Valley, CA (US); Rajiv Shah, Rancho Palos Verdes, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 12/405,840

(22) Filed: Mar. 17, 2009

(65) Prior Publication Data

US 2009/0177281 A1    Jul. 9, 2009

Related U.S. Application Data

(62) Division of application No. 11/026,678, filed on Dec. 31, 2004, which is a division of application No. 10/034,505, filed on Dec. 28, 2001, now Pat. No. 6,923,936.

(60) Provisional application No. 60/335,638, filed on Oct. 24, 2001, provisional application No. 60/335,978, filed on Oct. 23, 2001.

(51) Int. Cl.
| | |
|---|---|
| G01N 27/00 | (2006.01) |
| B08B 17/00 | (2006.01) |
| A61L 2/00 | (2006.01) |
| A61L 9/00 | (2006.01) |
| B05D 5/12 | (2006.01) |
| A61F 2/48 | (2006.01) |
| A61F 2/70 | (2006.01) |
| B65B 55/02 | (2006.01) |
| B65D 85/84 | (2006.01) |
| A61N 1/18 | (2006.01) |
| G01F 1/64 | (2006.01) |

(52) U.S. Cl. ............ 422/1; 422/56; 422/82.01; 422/98; 422/6; 422/22; 422/2; 422/4; 422/121; 422/186; 422/292; 422/186.05; 422/300; 422/305; 422/905; 427/74; 427/282; 623/24; 623/25; 623/26; 53/425; 53/431; 206/524.1; 607/6; 205/779

(58) Field of Classification Search ............ 422/56, 422/82.01, 98, 1, 6, 22, 2, 4, 121, 186, 292, 422/186.05, 300, 305, 905; 427/74, 282; 623/24–26; 53/425, 431; 206/524.1; 607/6; 205/779
See application file for complete search history.

(56) References Cited

U.S. PATENT DOCUMENTS 4,680,268 A    7/1987    Clark, Jr.
(Continued)

FOREIGN PATENT DOCUMENTS

DE            43 31 934 C1    5/1995
(Continued)

OTHER PUBLICATIONS

PCT Search Report dated Jan. 10, 2003 from PCT application No. PCT/US02/30944.
(Continued)

*Primary Examiner*—Jill Warden
*Assistant Examiner*—Monzer R. Chorbaji
(74) *Attorney, Agent, or Firm*—Foley & Lardner LLP

(57) ABSTRACT

A sterile device immersed in a sterile buffer and a method for providing same. The sterile device may be a medical device such as a biosensor having a biomolecule as a sensing element such as, for example, a glucose oxidase enzyme. The buffer may be a bicarbonate solution. Both the device and the buffer may be packaged and stored over long term while maintaining sterilization. The sterilization method may comprise a combination of gaseous, liquid and light sterilization.

8 Claims, 10 Drawing Sheets

U.S. PATENT DOCUMENTS

| | | | |
|---|---|---|---|
| 4,798,611 A | 1/1989 | Freeman, Jr. | |
| 4,863,016 A | 9/1989 | Fong et al. | |
| 4,877,964 A | 10/1989 | Tanaka et al. | |
| 5,143,617 A | 9/1992 | Grabenkort | |
| 5,391,463 A | 2/1995 | Ligler et al. | |
| 5,421,981 A * | 6/1995 | Leader et al. | 204/403.13 |
| 5,786,598 A | 7/1998 | Clark et al. | |
| 5,914,026 A * | 6/1999 | Blubaugh et al. | 600/347 |
| 5,925,885 A | 7/1999 | Clark et al. | |
| 5,989,498 A | 11/1999 | Odland | |
| 6,387,379 B1 | 5/2002 | Goldberg et al. | |
| 6,599,268 B1 | 7/2003 | Townsend et al. | |

FOREIGN PATENT DOCUMENTS

| | | |
|---|---|---|
| JP | 60-204847 | 2/1985 |
| JP | 02-068065 | 3/1990 |
| JP | 04-053561 | 2/1992 |
| JP | 2000-095209 | 4/2000 |
| JP | 2000-511497 | 9/2000 |
| JP | 2002-017826 | 1/2002 |
| WO | WO 93/03362 | 2/1993 |
| WO | WO 96/05869 | 2/1996 |
| WO | WO 00/49940 | 8/2000 |

OTHER PUBLICATIONS

European Search Report dated Feb. 28, 2005 from related European Patent Application No. 02763783.4-2113-US0230944.

Office Action dated Sep. 27, 2004 from related U.S. Appl. No. 10/034,505.

Office Action dated Jun. 26, 2009 from related U.S. Appl. No. 11/026,678.

Final Office Action dated Jan. 9, 2009 from related U.S. Appl. No. 11/026,678.

U.S. Office Action dated May 13, 2009 from related U.S. Appl. No. 11/026,678.

Notice of Allowance from related Japanese patent application No. 2003-537681.

JP Office Action for Application No. 2003-537681 dated Nov. 18, 2008.

US Notice of Allowance for U.S. Appl. No. 10/034,505 dated Feb. 25, 2005.

US Office Action for U.S. Appl. No. 11/026,678 dated Aug. 21, 2009.

* cited by examiner

STERILE DEVICE AND METHOD FOR PRODUCING SAME

CROSS-REFERENCE TO RELATED APPLICATIONS

This application is a divisional of U.S. application Ser. No. 11/026,678, filed Dec. 31, 2004, entitled "Sterile Device And Method For Producing Same," herein incorporated by reference in its entirety and is a basis for priority. U.S. application Ser. No. 11/026,678 is a divisional of U.S. application Ser. No. 10/034,505, filed Dec. 28, 2001, now U.S. Pat. No. 6,923,936, herein incorporated by reference in its entirety and is a basis for priority, and which in turn claims the benefit of priority from U.S. Provisional Application Ser. No. 60/335,978, filed Oct. 23, 2001 and U.S. Provisional Application Ser. No. 60/335,638 filed Oct. 24, 2001. The entirety of each application is incorporated herein by reference.

BACKGROUND

1. Field of the Invention

The present invention relates to the field of device sterilization and, in particular, to the sterilization of in vivo medical devices.

2. Description of Related Art

Device sterilization is a routine and necessary step in the manufacture of products in the medical, pharmaceutical, plastic, cosmetic and food industries as well as other industries. Device sterilization facilitates aseptic introduction of a device into its intended environment. For example, in the field of medical devices, where some devices may be used in sterile environments such as, for example, operating rooms or where some devices may be utilized in vivo, such as, for example, physiological parameter sensors, device sterilization aids in the elimination of deleterious microorganisms from the human body environment, reducing the risk of infection and disease.

Traditional device sterilization has been performed in a variety of ways. For example, in the medical device area, ethylene oxide (EtO) sterilization has been an effective sterilant for the elimination of microorganisms from medical devices. Being a gas, EtO may permeate an entire structure, resulting in three-dimensional sterilization of a device. However, EtO is a highly toxic gas and can have a damaging effect on certain products. For example, biosensors typically utilize a biomolecule as a sensing element. Exposure of a biomolecule to EtO may substantially reduce the long-term stability and sensitivity of the biomolecule, making EtO undesirable as a sterilant for biomolecular sensing elements.

Other sterilants are also available and in wide use for device sterilization. For example, glutaraldehyde is used extensively as a disinfectant for equipment in the medical and dental industries. Glutaraldehyde is commonly supplied as an aqueous solution and, when used as such, provides for bulk sterilization of equipment. In addition, if the device being sterilized is a biosensor having a biomolecule as a sensing element, glutaraldehyde typically does not produce any damaging effects on the biomolecule. However, being supplied as an aqueous solution, glutaraldehyde, as well as other aqueous sterilants, may not be able to permeate portions of devices that have been sealed for protection. For example, if a portion of a sensor houses electronics, the electronics may be enclosed in a housing impervious to fluids so that introduction of a fluid to the electronic housing does not result in the short circuiting of the electronics. In such a situation, glutaraldehyde or other aqueous sterilants are ineffective to sterilize the device.

When gaseous or liquid sterilants have proven ineffective to sterilize the devices in question, industry has turned to other methods of sterilization. For example, radiation sterilization using gamma or electron-beam radiation is sometimes effective but can destroy sensitive components upon application. For example, radiating devices that contain integrated circuits that have not been radiation hardened may damage the integrated circuits, rendering the devices inadequate for their intended purposes.

Steam sterilization may also be sometimes effective, but devices being sterilized by steam must be able to withstand high temperatures and condensation that are a natural byproduct of the steam process. Many devices cannot withstand such an environment.

SUMMARY OF THE DISCLOSURE

Embodiments of the present invention relate to processes for sterilizing devices and the resultant sterile device.

Embodiments of the present invention include, without limitation, a sterile apparatus comprising a sterile buffer for hydration and a sterile device for use in a sterile application immersed in the sterile buffer. A sterile package may enclose the sterile device and the sterile buffer. The sterile device may be a medical device, such as a sensor. The sensor may include a hydrated element and may comprise a biomolecule, such as a glucose oxidase enzyme. Alternative embodiments may omit the sterile buffer and hydration of the medical device, such that a sterile package encloses a medical device.

Moreover, the sterile device may be implantable. The sterile device may come packaged in a transparent, translucent, or otherwise optically transmissive package. The sterile device, sterile buffer and sterile package may be sterilized using light. The sterile device may also be sterilized using a gas or a liquid.

Embodiments of the present invention may also include a method for sterilizing an apparatus comprising placing the apparatus in a buffer, enclosing the apparatus and the buffer in a package and sterilizing the package using light. The method may further comprise sterilizing the apparatus in a gas and a liquid. The light used for sterilizing the package may be a broad spectrum pulse light. The gas used for sterilizing the apparatus may be ethylene oxide. The liquid used for sterilizing the apparatus may be glutaraldehyde.

The buffer into which the apparatus is placed may be a bicarbonate solution. In addition, the apparatus placed into the buffer may be a biosensor having a biomolecule such as, for example, a glucose oxidase enzyme as a sensing element.

Further embodiments of the present invention include a sterile, implantable medical device for in vivo implantation including a sterile electronic circuit, a sterile biological molecule for use as an agent in generating a signal to be used by the sterile electronic circuit, and a sterile reservoir for housing the sterile biological molecule. The device may also include a sterile package for packaging the device. The package may be optically transmissive. The device may be packaged in a wet, sterile buffer solution. The device does not need to be rinsed before implantation.

The biological molecule may be a sensor matrix protein and the electronic circuit may be an integrated circuit. Further, the reservoir may be a polymer and a permeable window may cover the biological molecule. The device may be used for in vivo implantation without an acclimation period.

Embodiments of the present invention may also include a method for producing a sterile, implantable medical device for in vivo implantation including preparing a device substrate for sterilization, affixing non-biological elements to the substrate, sterilizing the non-biological elements and the substrate with a gaseous sterilant, affixing biological elements to the substrate, sterilizing the biological elements with a wet sterilant, packaging the substrate, the non-biological and biological elements into a wet buffer, and sterilizing the substrate, the non-biological and biological elements packaged in the wet buffer using light. Sterilizing the non-biological elements and the substrate with a gaseous sterilant may include sterilizing the non-biological elements and the substrate with ethylene oxide. The biological elements may be affixed to the substrate after sterilizing the non-biological elements and the substrate with a gaseous sterilant. Sterilizing the biological elements with a wet sterilant may include sterilizing the biological elements with glutaraldehyde. Sterilizing the substrate, the non-biological and biological elements packaged in the wet buffer using light may include sterilizing the substrate, the non-biological and biological elements packaged in the wet buffer using a broad spectrum pulse light.

Moreover, sterilizing the biological elements with a wet sterilant may include preparing a sterilization chamber, preparing the wet sterilant, pre-warming the wet sterilant, loading sensors into the chamber, exposing the sensors to the wet sterilant, rinsing the sensors a first time, and rinsing the sensors a second time. Rinsing the sensors a first time and a second time may include rinsing the sensors with a bicarbonate buffer. The method may further include implanting the device in vivo. The device may be implanted in vivo without rinsing.

These and other objects, features, and advantages of embodiments of the invention will be apparent to those skilled in the art from the following detailed description of embodiments of the invention when read with the drawings and appended claims.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Figure 1:
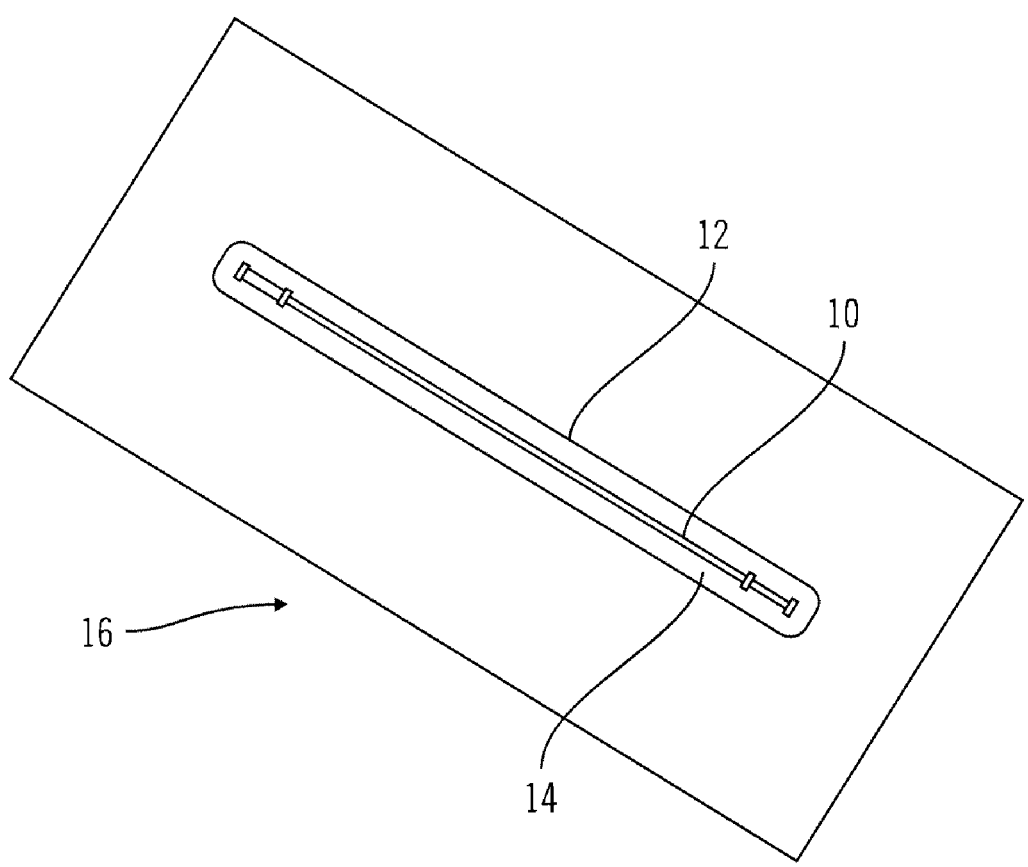
FIG. 1 shows a perspective view of a sterile device immersed in a sterile buffer according to an embodiment of the present invention.

FIG. 1 shows a sterile device immersed in a sterile buffer according to an embodiment of the present invention. Sterile device 10 may be enclosed within a tube 12 and surrounded by a sterile buffer 14. The tube 12 may be part of a larger package 16.

The sterile device 10 may be any of a variety of devices, such as, for example, a medical device. The sterile device 10 may be a sensor such as, for example, a physiological parameter sensor, or may be another therapeutic or diagnostic device. The sterile device 10 may also be other medical devices, medical components or medical implants such as, for example, drug delivery systems or replacement devices. For example, the sterile device 10 may be a heart valve, such as an artificial heart valve or a heart valve made from biological materials. The sterile device 10 may also be other biological materials used for in vivo implantation. The sterile device 10 may also be medical devices such as, for example, pacemakers or pacemaker leads. The sterile device 10 may also be a medical device such as for example, a spinal implant. The spinal implant may be, for example, a screw. The sterile device 10 may be a medical device, for example, with or without a biological element. The sterile device 10 may be any medical device, for example, used for implantation in a body.

Some devices, such as, for example, medical devices, may require hydration. For example, if the sterile device 10 is an in vivo biosensor, the sensing element of the biosensor may be a biomolecule that cannot dehydrate without losing its effectiveness, thus requiring hydration during storage. In addition, the in vivo biosensor must be sterile before being implanted into a human or animal. Using embodiments of the present invention, the biomolecule may be stored in a hydrated environment, i.e., the sterile buffer 14, while maintaining sterilization adequate for implantation into a human or animal.

The tube 12 within which the sterile device 10 may be enclosed may be of sufficient size to enclose the sterile device 10 and the sterile buffer 14 in which the sterile device 10 is immersed. In order to effect sterilization according to embodiments of the present invention, the tube 12 may be transparent, translucent or made of any material that is optically transmissive or that passes light adequate to sterilize the device 10 and the buffer 14. For example, the tube 12 may be made from a transparent plastic.

The sterile buffer 14 may be any solution that is chemically inert with respect to the sterile device 10. In other words, any sterile buffer 14 may be utilized in embodiments of the present invention that does not harm the sterile device 10 or, in an embodiment where the sterile device 10 is a sensor having a biomolecule as a sensing element, does not compromise the efficacy of the sensing element. For example, the sterile buffer 14 may be a bicarbonate solution.

The package 16 may be part of the tube 12 or may be separate from the tube 12 but attached to it. The package 16 may be made from a variety of materials, such as, for example, plastic.

The level of sterilization needed for a device, buffer, package or other component of an embodiment of the present invention to be considered sterile depends on its intended purpose. For example, the Food and Drug Administration (FDA) sets sterilization levels for physiological parameter sensors being implanted into a human being. Thus, if the intended purpose of a physiological parameter sensor is for implantation into a human being, the level of sterilization should meet FDA levels. For other uses, sterilization levels may be higher or lower than that for physiological parameter sensors being implanted into a human being depending on the application.

Figure 2:
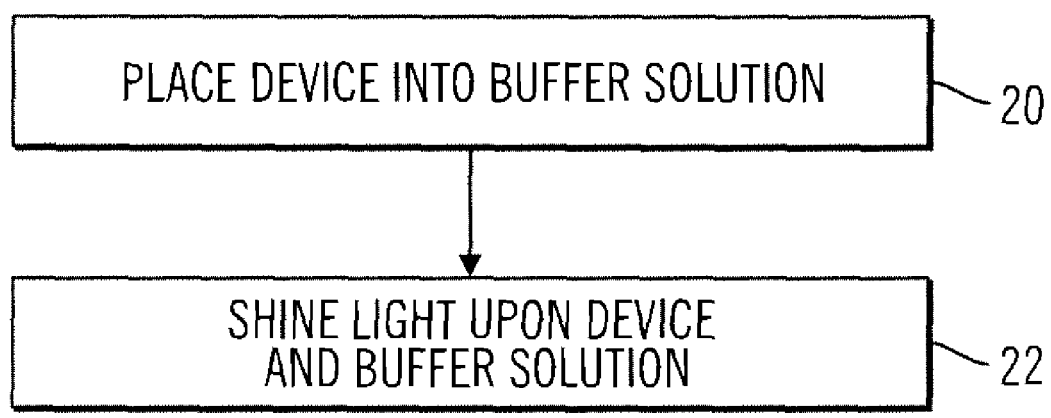
FIG. 2 shows a generalized method for producing a sterile device immersed in a sterile buffer according to an embodiment of the present invention.

FIG. 2 shows a generalized method for producing a sterile device immersed in a sterile buffer. At step 20, a device may be septically or aseptically placed into a buffer solution. The device and the buffer solution may subsequently be sealed in a container made from a material capable of passing an amount of light adequate for sterilization.

At step 22, a light may be shined upon the device and the buffer solution. The spectrum and intensity of the light should be sufficient to sterilize the device and the buffer solution to the desired level of sterilization. For example, according to an embodiment of the present invention, sterilization of a device immersed in a buffer solution requires that the number of living organisms within the device and the buffer solution subsequent to sterilization be no greater than 1 out of $1\times10^6$ organisms. The light may be a broad spectrum pulse light (BSPL) and may include light having wavelengths of 300 nm or smaller. The light may have spectrum and wavelength characteristics adequate to perform surface sterilization of the package, the device and the buffer. Accordingly, the packaging used should be of sufficient optical transmissivity to pass the light used for sterilization.

According to an alternative embodiment of the present invention, a package may enclose a sterile device without a sterile buffer and without hydration of the device. The package and the device may be subjected to a light sufficient to sterilize the package and the device.

Figure 3:
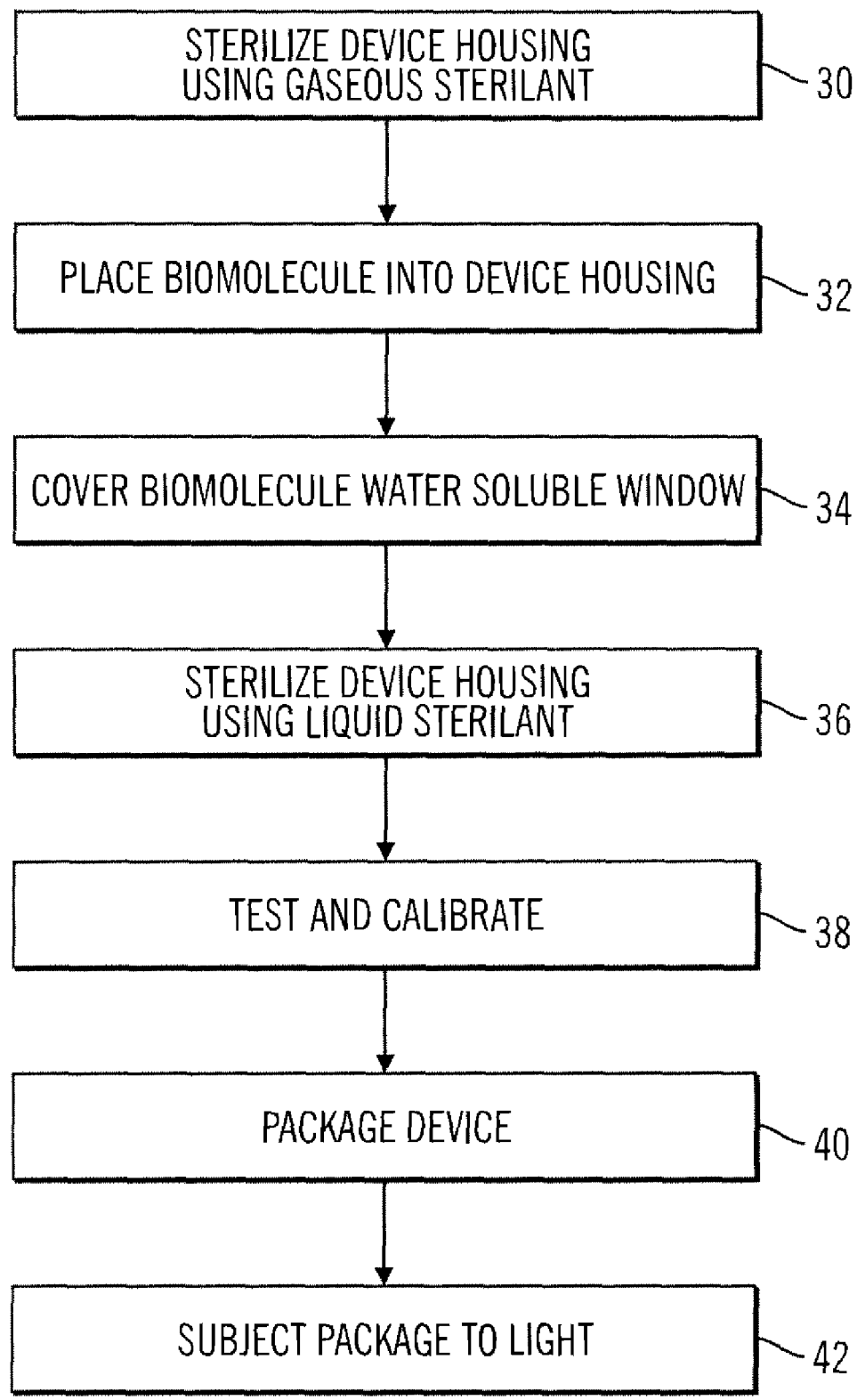
FIG. 3 shows a detailed method for producing a sterile device immersed in a sterile buffer according to an embodiment of the present invention.

FIG. 3 shows a more detailed method for producing a sterile device immersed in a sterile buffer. At step 30, a device housing is sterilized using a gaseous sterilant, such as, for example, EtO. The device housing is fabricated such that, at the time of sterilization using a gaseous sterilant, the device housing does not contain a biomolecule such as, for example, an enzyme, antibodies or DNA, or any other element that would be compromised by exposure to the gaseous sterilant. For example, if the device being sterilized is a sensor and the sensing element of the sensor is an enzyme, such as, for example, glucose oxidase (GOx), the sensor may be fabricated without the GOx enzyme, then subjected to EtO sterilization. By so doing, the sensor housing and all other elements associated with the sensor that are not compromised by exposure to EtO may be sterilized without detriment to the GOx enzyme.

A gaseous sterilant may be applied to a device for which sterilization is desired in a variety of ways. For example, a device may be put into an environmental chamber suitable for the gaseous sterilant being used and the chamber may be evacuated to remove any unwanted gases in the chamber. Then, the gaseous sterilant may be released into the chamber in a volume sufficient to encompass, permeate and sterilize the device.

The efficacy of the gaseous sterilant may be determined in a variety of ways. For example, biological indicators may be sterilized along with a device housing and used to determine the level of sterilization. Biological indicators may be in the form of living organisms contained in vials. The vials containing the living organisms may be placed into a chamber or other environment along with the device to be sterilized and subjected to the gaseous sterilant. Subsequent to exposure to the gaseous sterilant, the vials may be checked and the number of organisms still living, if any, determined. For example, according to an embodiment of the present invention, if no more than one organism out of one million organisms remain living after exposure to gaseous sterilant, the device may be considered adequately sterilized for in vivo analysis.

Figure 4:
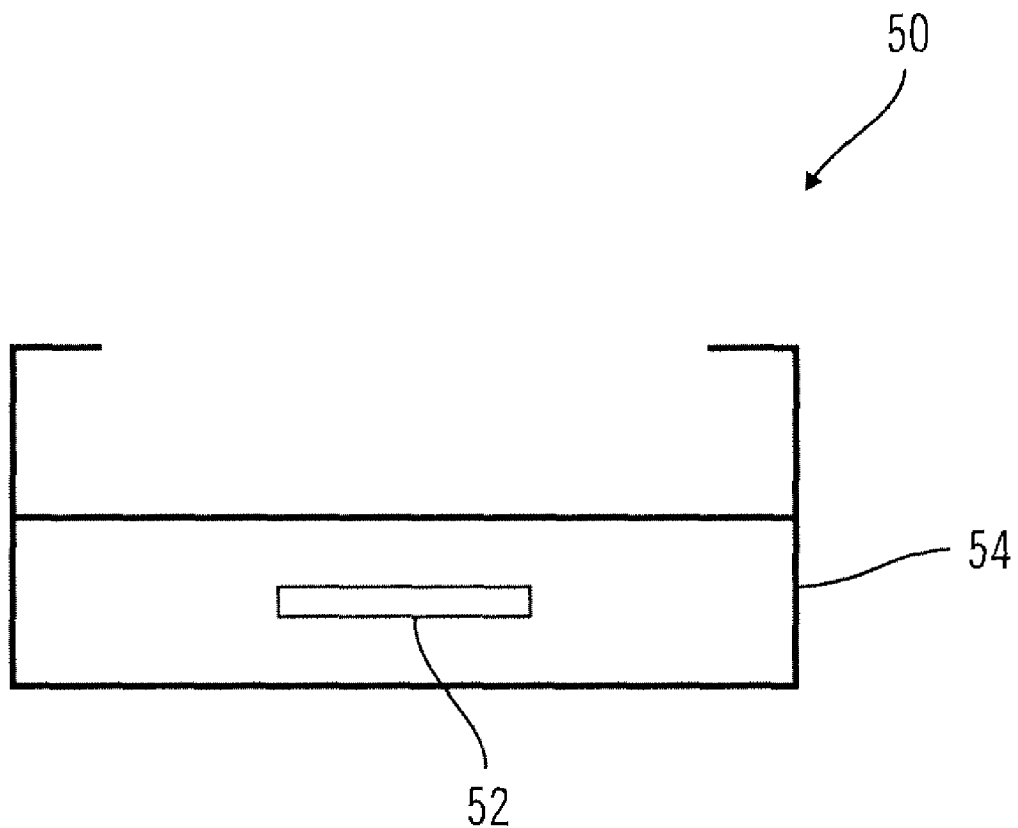
FIG. 4 shows a side view of a portion of a sensor for which sterilization is desired according to an embodiment of the present invention.

FIG. 4 shows a portion of a sensor 50 which has been prepared for gaseous sterilization according to an embodiment of the present invention. The sensor 50 may be a combination of electronics 52 and a sensing element (not shown). For example, the sensor 50 may be comprised of a substrate, one side of which contains sensor electronics and the other side of which contains a sensing element. In FIG. 4, the sensing element, which may be a biomolecule such as GOx, for example, has not yet been inserted into the sensor 50. However, the sensor electronics 52 have been placed into the sensor and are surrounded by a gas permeable housing 54. The sensor electronics 52 may be exposed to a gaseous sterilant without consequence to the proper operation of the electronics.

The gaseous sterilant used at step 30 may be substituted with other sterilants. For example, radiation may be used. The device may be subjected to gamma radiation, for example for sterilization. However, radiation may have a deleterious effect on elements within the device. For example, if there are integrated circuits on the device, gamma radiation may destroy the integrated circuits unless they have been certified as radiation hardened.

Returning to FIG. 3, subsequent to gaseous sterilization, any element that would have been compromised by exposure to EtO may now be placed into the device housing at step 32. For example, if the device is a biosensor using a biomolecule as a sensing element, the biomolecule may be placed into the sensor at this time. The biomolecule may be immobilized onto a water soluble support and inserted, either septically or aseptically, into the device housing. If desired, at step 34 the biomolecule may also be covered with a water soluble window such as, for example, a hydrogel or some other type of water soluble membrane through which a fluid may pass in order to make contact with the biomolecule.

Figure 5:
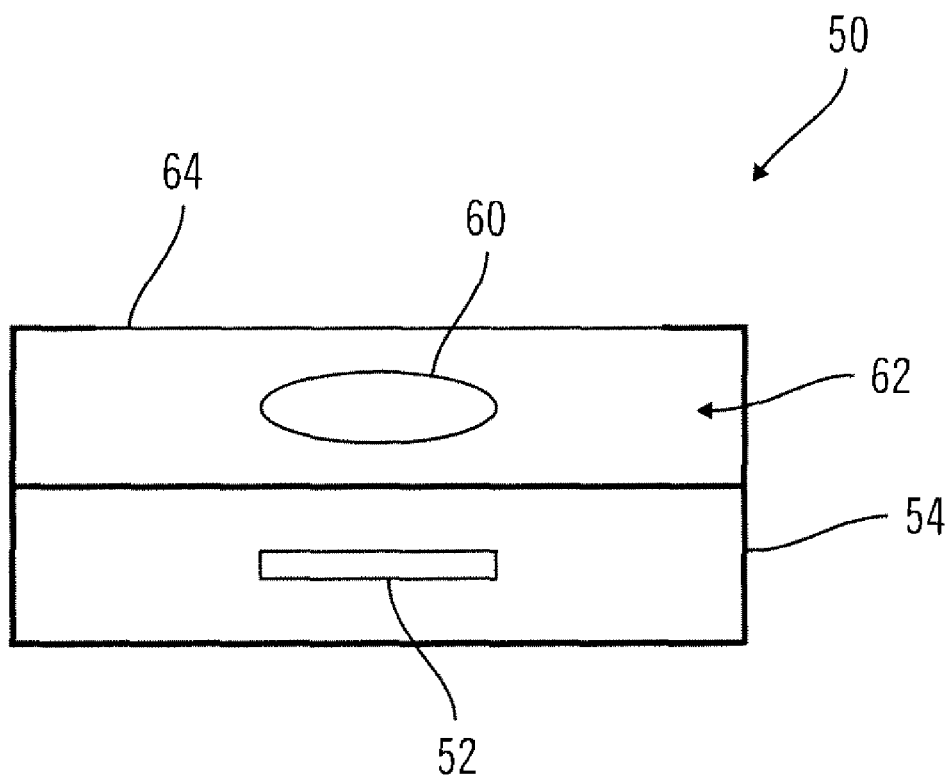
FIG. 5 shows another side view of a portion of a sensor housing for which sterilization is desired according to an embodiment of the present invention.

At step 36, the device housing may be sterilized using a liquid sterilant such as, for example, glutaraldehyde. The liquid sterilant may completely penetrate the housing and any element placed into the housing subsequent to gaseous sterilant exposure. For example, in the case of the biomolecule, the liquid sterilant may pass through the hydrogel window, penetrate the water soluble support onto which the biomolecule is immobilized and contact the biomolecule, sterilizing the hydrogel window, the water soluble support and the biomolecule. A sensor 50 having electronics 52 and a biomolecule 60 immobilized onto a water soluble support 62 and covered by a hydrogel window 64 may be seen in FIG. 5.

The liquid sterilant may be applied to the device in a variety of ways. For example, the device may be placed into a chamber, such as, for example, a cylindrical column and the liquid sterilant may subsequently be introduced into the cylindrical column. Many liquid sterilants are readily available commercially, such as, for example, glutaraldehyde, phenol or formaldehyde. In addition, any type of bactericidal agent may be used as a liquid sterilant.

If glutaraldehyde is used as a liquid sterilant, it may be used in concentrations from about 2.5% to about 25%. Heat may also be applied during the liquid sterilization phase to accelerate infusion of the liquid sterilant into the device and its elements. Also, if glutaraldehyde is used as a liquid sterilant, the device may be rinsed with a sterile rinse solution subsequent to sterilization.

At step 38, the device may be tested and calibrated. Because the device has passed through a gaseous sterilization step and a liquid sterilization step up to this point, all testing and calibration of the device may be done in an aseptic environment using sterilized equipment so as not to compromise the integrity of the sterilization up to this point.

At step 40, the device may be packaged. The package may be translucent or transparent, or may have some level of optical transmissivity. In addition, the package may be sealed hermetically or sealed in such a manner that it is impervious to external contamination and adequate to maintain the sterility of a sterile device in a sterile buffer. The sterile device may be encapsulated in the package and immersed in a sterile buffer, such as, for example, a bicarbonate buffer. By immersing the sterile device into a sterile buffer, the sterile device may stay hydrated without becoming contaminated. Thus, according to embodiments of the present invention, devices that require sterilization and hydration may be sterilized and immersed in a hydrating buffer fluid without compromising the integrity of the sterilization. Accordingly, whereas prior art devices may require re-sterilization after being stored in a buffer or other hydrating fluid, devices sterilized according to embodiments of the present invention may be used in a sterile environment directly out of the package, without the need to re-sterilize the device.

For example, if the device requiring sterilization is an implantable, physiological parameter sensor having electronics for signal processing and a biomolecule as a sensing element, the entire sensor and any associated components such as, for example, a sensor lead and a connector, may, after gaseous and liquid sterilization, be encapsulated in a container and immersed in a sterile buffer. In the case where the biomolecule is placed under a water soluble window such as, for example, a hydrogel window, the window may require hydration up to the point where it is implanted in vivo to prevent dehydration and cracking. Using embodiments of the present invention, the sensor and other components may remain packaged in a buffer solution without contamination, thereby maintaining the hydration of the hydrogel window and, consequently, the viability of the sensor, without further need to re-sterilize the sensor after opening the package.

At step 42, the package, including, without limitation, the device and the sterile buffer, may be subjected to light for a final sterilization. The light may be a broad spectrum pulse light (BSPL) and may include light having wavelengths of 300 nm or smaller. The light may have spectrum and wavelength characteristics adequate to perform surface sterilization of the package, the device and the buffer. Accordingly, the packaging used in step 40 should be of sufficient optical transmissivity to pass the light used for sterilization. For example, PURE BRIGHT light by Maxwell Industries may be used as a BSPL.

Figure 6A:
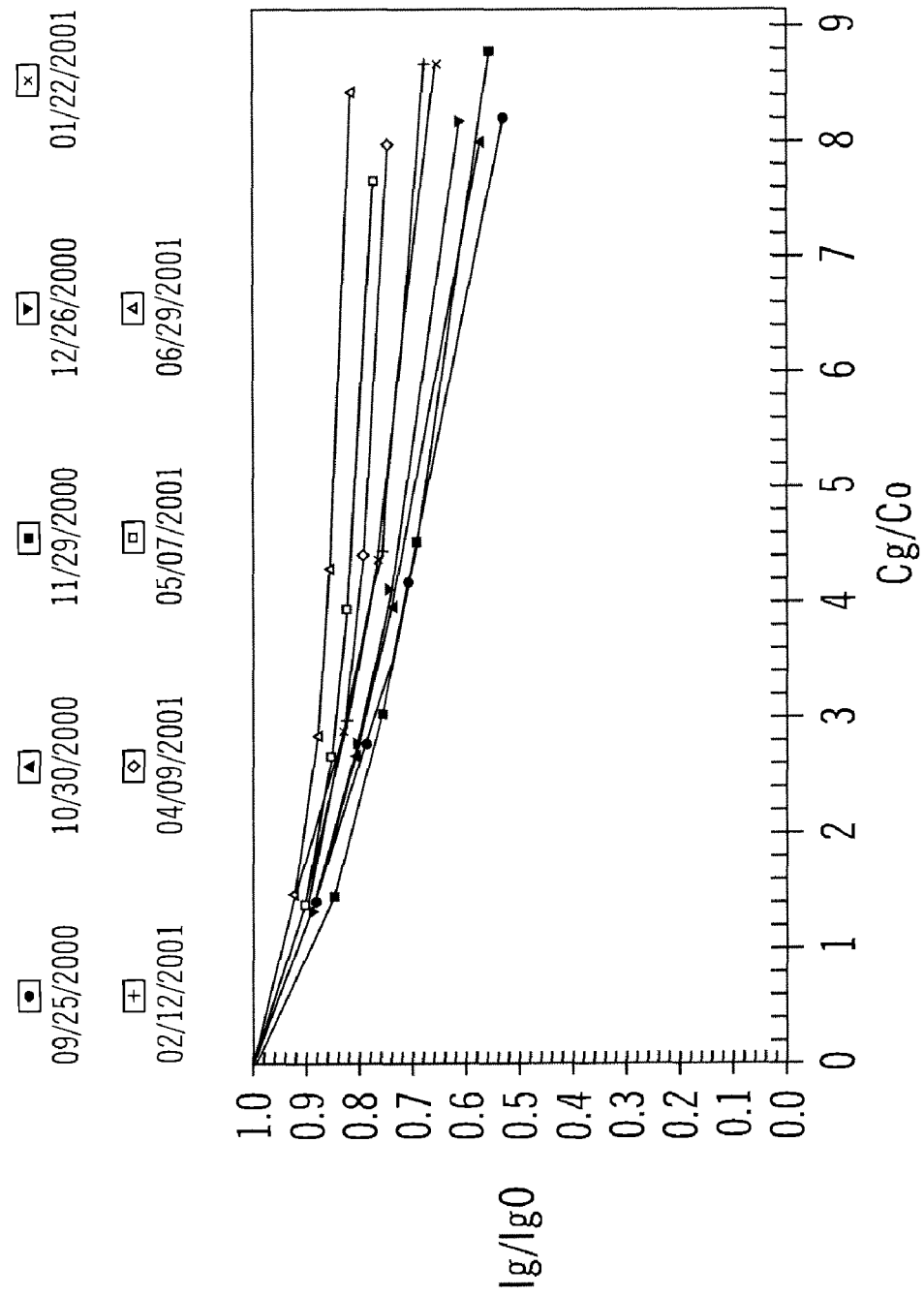
FIG. 6A shows graphical data for a sensor subjected to an EtO sterilization process according to the prior art.
Figure 6B:
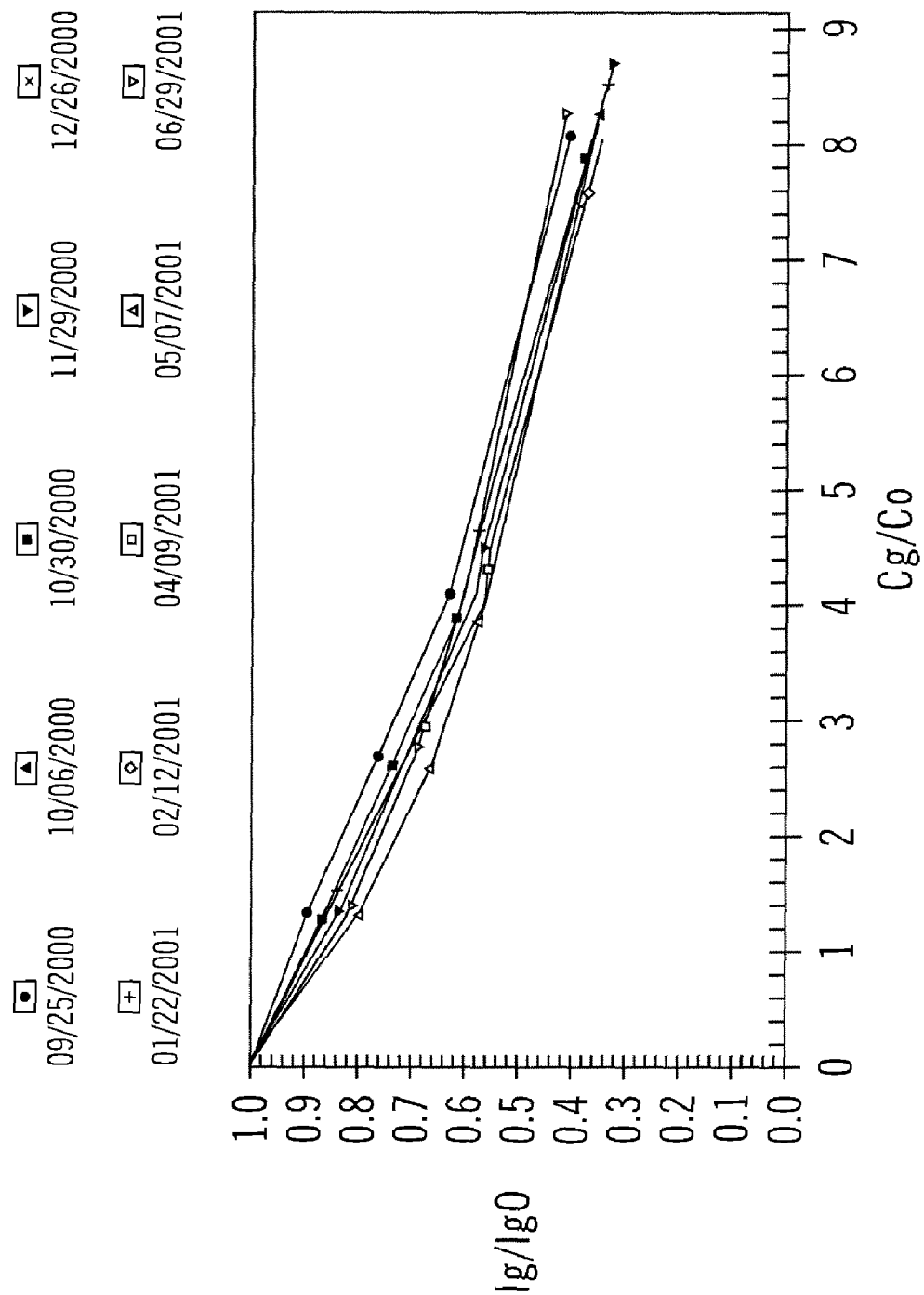
FIG. 6B shows graphical data for a sensor subjected to a sterilization process according to embodiments of the present invention.

Subsequent to step 42, the sterile device immersed in the sterile buffer may be stored or stocked for extended lengths of time. Using embodiments of the present invention, devices having sensitive elements such as, for example, an implantable, physiological parameter sensor having a biomolecule as a sensing element, do not suffer the deleterious effects of EtO sterilization, yet an entire sensor assembly including, without limitation, a biomolecule such as, for example, a protein, an enzyme, antibodies, DNA or other biomolecule, may be sterilized to an extent suitable for in vivo implantation of the sensor. A comparison of a sensor having a biomolecular sensing element that has been sterilized by exposing the sensor and the biomolecule to EtO only to a sensor having a biomolecular sensing element that has been sterilized according to embodiments of the present invention may be seen in FIGS. 6A and 6B. FIGS. 6A and 6B show sensor current versus concentrations of glucose to oxygen. As can be seen, the stability of the biomolecule sterilized according to embodiments of the present invention shown in FIG. 6B is greater than that of the biomolecule that has been exposed to EtO shown in FIG. 6A.

A sterilization process according to an embodiment of the present invention may be used with a variety of devices in a variety of manufacturing environments. For example, a sterilization process according to an embodiment of the present invention may be used with sensors such as, for example, physiological parameter sensors, or may be used with other therapeutic or diagnostic devices. In addition, a sterilization process according to an embodiment of the present invention may be used with other medical devices, medical components or medical implants such as, for example, drug delivery systems or replacement devices. For example, a sterilization process according to an embodiment of the present invention may be used with heart valves, such as artificial heart valves or heart valves made from biological materials. A sterilization process according to an embodiment of the present invention may be used with other biological materials used for in vivo implantation. A sterilization process according to an embodiment of the present invention may be used with other medical devices such as, for example, pacemakers or pacemaker leads. A sterilization process according to an embodiment of the present invention may be used with a device such as, for example, a spinal implant. The spinal implant may be, for example, a screw. A sterilization process according to an embodiment of the present invention may be used with a medical device, for example, with or without a biological element. A sterilization process according to an embodiment of the present invention may be used with any medical device, for example, used for implantation in a body.

Figure 7:
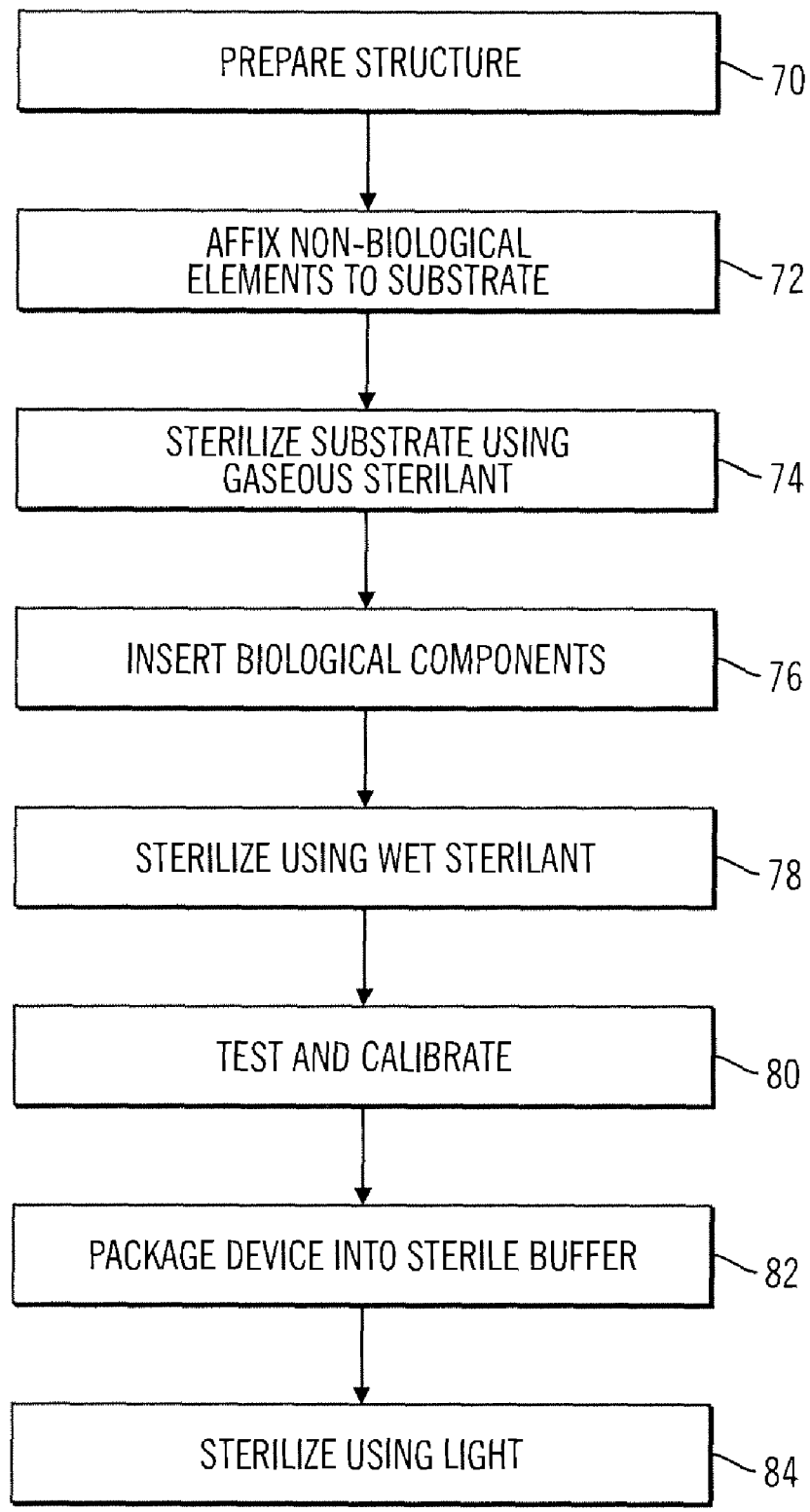
FIG. 7 shows a generalized sterilization process which advances in stages and is used in conjunction with a manufacturing process for producing sterile, implantable medical devices according to an embodiment of the present invention.

FIG. 7 shows a sterilization process according to an embodiment of the present invention which advances in stages and is used in conjunction with a manufacturing process that produces sterile, implantable medical devices. If, for example, the medical device produced is a physiological parameter sensor, the sterile, implantable medical device may be an integrated structure that includes microelectronics, a polymeric reservoir and a matrix of biological molecules contained in the reservoir for therapeutic or diagnostic applications. A matrix of biological molecules and a method of formulating a matrix of biological molecules may be found in Applicant's concurrent application entitled "METHOD FOR FORMULATING A GLUCOSE OXIDASE ENZYME WITH A DESIRED PROPERTY OR PROPERTIES AND A GLUCOSE OXIDASE ENZYME WITH THE DESIRED PROPERTY," which is hereby incorporated by reference herein.

At step 70, a structure substrate may be manufactured in a manner suitable for housing microelectronics and a matrix of biological molecules. For example, the substrate may be made of a ceramic or other material and may be fabricated to house components on either of its sides. At step 72, microelectronics may be affixed to one side of the substrate while a reservoir for housing a matrix of biological molecules may be affixed to another side of the substrate. The reservoir may be a polymer such as, for example, silicone.

At step 74, the substrate containing the microelectronics and the reservoir may be sterilized utilizing a gaseous sterilant. In addition, any non-biological elements of the device may be affixed to the substrate and subjected to gaseous sterilization. The matrix of biological molecules is not inserted into the device at this time so that the deleterious effects of the gaseous sterilization do not compromise the integrity of the biological molecules. For example, if the substrate is sterilized using EtO and the biological molecule is a GOx enzyme, the harsh nature of the EtO may compromise the long term stability of the GOx enzyme. Thus, only non-biological elements of the device are sterilized during the gaseous sterilization stage. The non-biological elements of the device may be sterilized to levels suitable for in vivo implantation determined by the FDA.

Subsequent to gaseous sterilization, the manufacturing of the device may continue with insertion of the biological components into the reservoir of the device at step 76. For example, a GOx enzyme or other biological element such as, for example, a sensor matrix protein, may be inserted into the reservoir at this time. Because the device has already been subjected to gaseous sterilization using, for example, EtO, there is no risk to the enzyme that its stability characteristics will be compromised due to exposure to a gaseous sterilant. After the biological molecule has been inserted into the reservoir, the reservoir may be enclosed with a permeable window which may separate the biological molecule from the surrounding environment. The permeable window may be liquid permeable.

At step 78, the device, which at this stage of the manufacturing process according to an embodiment of the present invention includes, without limitation, a substrate having microelectronics, a reservoir, and a biological molecule or a matrix of biological molecules, may be sterilized using a wet sterilant. In addition, any other biological elements of the device may be included with the device for sterilization using a wet sterilant. For example, the device, included, without limitation, any biological components of the device, may be sterilized using glutaraldehyde or other wet sterilant. The biological elements of the device may be sterilized to levels suitable for in vivo implantation determined by the FDA.

Figure 8:
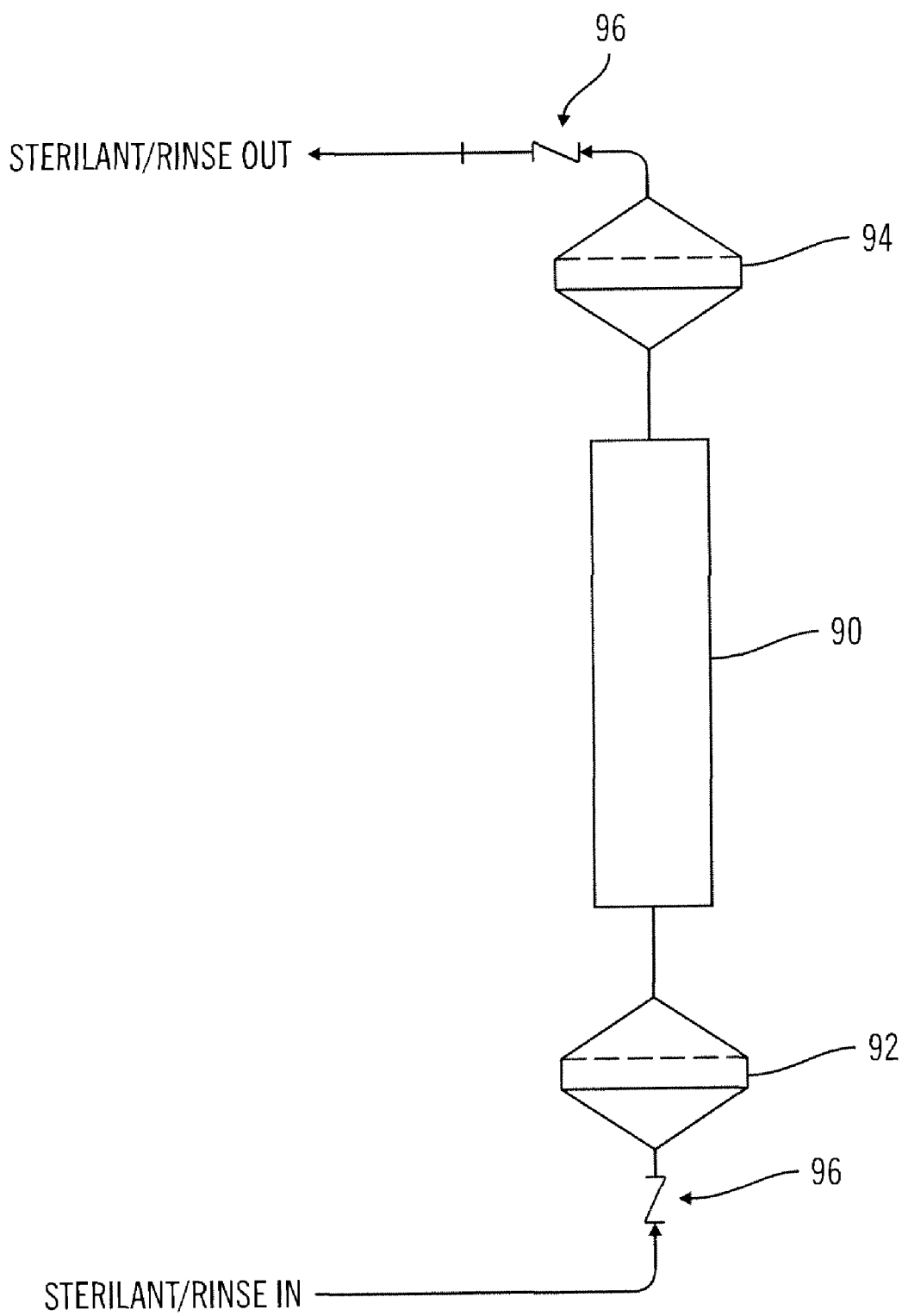
FIG. 8 shows a system for wet sterilizing a device containing biological elements according to an embodiment of the present invention.

A system for wet sterilizing a device containing biological elements according to an embodiment of the present invention is shown in FIG. 8. A pressurized sterilant/rinse reservoir (not shown) may be connected to a chromatography column 90. An inlet of the chromatography column 90 may be fitted with an inlet filter housing 92 and an outlet of the chromatography column 90 may be fitted with an outlet filter housing 94. The filter housings 92, 94 may accommodate filters. Check-valves 96 may be located before the inlet filter 92 and after the outlet filter 94. The check-valves 96 prevent backflow out of and back into the sterilizing chamber. The chromatography column 90 may be water-jacketed to allow temperature control of the sterilization process.

Flow through the system shown in FIG. 8 may be provided by nitrogen pressurization of the reservoir. The pressurization drives the liquid through the filters and into the sterilizing chamber.

Figure 9:
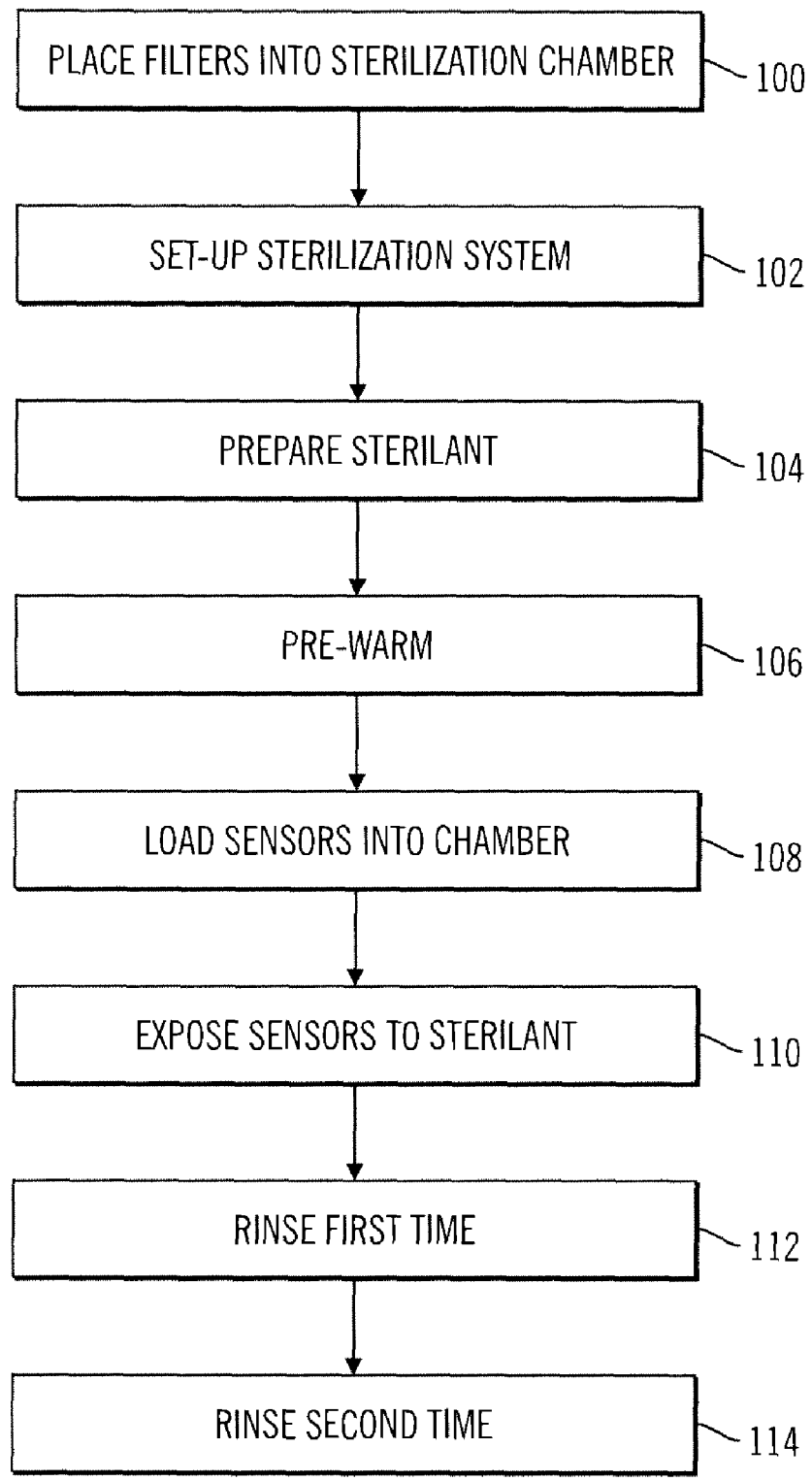
FIG. 9 shows a detailed process for wet sterilization of a device according to an embodiment of the present invention.

FIG. 9 shows a more detailed process for wet sterilization of the device according to an embodiment of the present invention. At step 100, filters may be placed into a sterilization chamber and the sterilization chamber may be prepared. Preparation of the sterilization chamber may include, without limitation, ensuring that the filter housings are tight.

At step 102, the sterilization system may be set up. Depending on the sterilization system used, set up of the system may include, without limitation, attaching, water lines, attaching thermometers, and attaching inlet and outlet lines.

At step 104, the sterilant solution may be prepared. For example, according to an embodiment of the present invention, 50 ml of concentrated bicarbonate buffer may be added to a clean 1000 ml graduated cylinder. A quantity of water may be added to the 50 ml of concentrated bicarbonate buffer to make 900 ml. The buffer solution may then be poured into a reservoir of the sterilization system. One hundred milliliters of 25% glutaraldehyde may be added to the reservoir. The sterilant solution may then be mixed.

At step 106, the sterilant may be pre-warmed. The chamber may be filled by applying both pressure and vacuum. The sterilant may be pre-warmed to 35-39 C. Pre-warming of the sterilant enhances the efficacy of the sterilization process.

At step 108, the sensors may be loaded into the chamber. The chamber may be closed and filled with the sterilant in the reservoir. At step 110, the sterilant exposure phase may be started. The sensors may be exposed to the sterilant for any amount of time necessary to achieve the desired sterilization. For example, the sensors may be exposed to the sterilant for a minimum of eight hours. During the exposure phase, any sterilant remaining in the reservoir may be discarded. A bicarbonate buffer solution of 50 ml of concentrated buffer per liter may be prepared and delivered into the reservoir.

At step 112, the sterilant may be rinsed a first time. The glutaraldehyde solution may be dumped and the sensors may be rinsed, for example, for a minimum of 15 minutes. At step 114, the sterilant may be rinsed a second time. The first rinse may be dumped and the rinse process may be repeated.

Returning to FIG. 7, at step 80 the device may be tested and calibrated. Because the device has passed through a gaseous sterilization step and a wet sterilization step up to this point, all testing and calibration of the device may be done in an aseptic environment using sterilized equipment so as not to compromise the integrity of the sterilization up to this point.

At step 82, the manufacturing process may continue by packaging the tested, calibrated device into sterile buffer solution. The sterile buffer solution may be a bicarbonate buffer. The package may be transparent or may have an optical transmissivity sufficient to pass a quantity of light sufficient for further sterilization.

At step 84, the package containing the buffer solution and the device, which, at this stage of the manufacturing process, includes, without limitation, all non-biological and biological elements, may be subjected to light for final sterilization. The light may be a BSPL. Both non-biological and biological elements of the device may be sterilized to levels suitable for in vivo implantation determined by the FDA. Light spectrum emitted during step 84 may by 200-1000 nm. The intensity of the light may be sufficient to disrupt normal cellular functions in microbes. According to an embodiment of the present invention, in order to achieve desired sterilization levels, eight lamps may be used per sensor. In addition, the lamps may be flashed three times per sensor.

In addition, biological indicators may be used during step 84 to verify that acceptance criteria for sterilization have been met. For example, according to an embodiment of the present invention, bacterial species common to sterilization microbiology such as, for example, *Bacillus pumilus, Bacillus stearothermophilus, Staphylococcus aureus* or *Pseudomonas aeruginosa*, may be injected into tubes, placed adjacent to the device being sterilized, and sterilized concurrently with the device. According to another embodiment of the invention, devices may be sterilized singly, in series. The tubes may be run before and after a device. The tubes may then be checked to ensure that they are negative for bacterial growth at the levels desired. For example, for in vivo implantation, bacterial growth should be at least as negative as required by the FDA for in vivo implantation.

Although the method according to an embodiment shown in FIG. 7 has sterilized a device using gaseous, wet and light steps, because the sterilization process according to embodiments of the present invention may be used in a variety of manufacturing environments, any number of sterilization steps may be included in the sterilization process. Thus, sterilization processes according to embodiments of the present invention are not limited to the process shown in FIG. 7.

Because the device has been packaged in a sterile buffer without long term deleterious effects to the stability of the biological molecule, no further sterilization is needed between removing the device from its package and in vivo implantation. The device may be used immediately without any acclimation period because, since the device is packaged in a sterile buffer, no rinsing is required before in vivo implantation because there is no glutaraldehyde or other sterilant on the device. Glutaraldehyde rinsing may take several hours, thus increasing surgical risk. Also, residual glutaraldehyde can cause blood clotting around the sensor, which could result in false readings. Using embodiments of the present invention, such issues associated with glutaraldehyde rinsing are minimized or eliminated. A physician may keep a packaged device in an operating room until it is time for implantation, at which time the package may be inserted and the device implanted in vivo.

A sterile, implantable device fabricated in stages according to an embodiment of the present invention provides enhanced long term stability for physiological parameter sensors as opposed to devices sterilized using EtO sterilization only. For example, devices sterilized using EtO sterilization only and having biological elements subjected to EtO may maintain calibrated current levels for approximately three months. In contrast, devices sterilized according to embodiments of the present invention, wherein non-biological elements are sterilized without biological elements, followed by sterilization of biological elements, followed by sterilization of both non-biological and biological elements, may remain stable for nine months to one year and longer.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A method of making a sterile, implantable medical device for in vivo implantation comprising:
    arranging an electronic circuit on a substrate;
    sterilizing the electronic circuit and the substrate with a first sterilization technique to provide a sterile electronic circuit and a sterile substrate;
    arranging a reservoir on the sterile substrate;
    arranging a biological molecule in the reservoir, the biological molecule for use as an agent in generating a signal to be used by the sterile electronic circuit; then
    sterilizing the biological molecule with a second sterilization technique, which is a different type of sterilization technique from the first sterilization technique, to provide a sterile biological molecule.

2. The method of claim 1, further comprising:
    arranging a permeable window covering the sterile biological molecule.

3. The method of claim 1, wherein the biological molecule is a sensor matrix protein.

4. The method of claim 1, further comprising:
    Packaging the device in a sterile package.

5. The method of claim 4, wherein the package is optically transmissive.

6. The method of claim 1, further comprising:
    Packaging the device in a wet, sterile buffer solution.

7. The method of claim 1, wherein the electronic circuit is an integrated circuit.

8. The method of claim 1, wherein the reservoir is a polymer.

* * * * *